(12) United States Patent
Prem

(10) Patent No.: US 6,422,990 B1
(45) Date of Patent: Jul. 23, 2002

(54) BLOOD PUMP FLOW RATE CONTROL METHOD AND APPARATUS UTILIZING MULTIPLE SENSORS

(75) Inventor: Edward K. Prem, Allison Park, PA (US)

(73) Assignee: Vascor, Inc., Pittsburgh, PA (US)

( * ) Notice: Subject to any disclaimer, the term of this patent is extended or adjusted under 35 U.S.C. 154(b) by 166 days.

(21) Appl. No.: 09/627,864

(22) Filed: Jul. 28, 2000

Related U.S. Application Data

(60) Continuation-in-part of application No. 09/273,384, filed on Mar. 22, 1999, which is a division of application No. 08/978,670, filed on Nov. 26, 1997, now Pat. No. 5,928,131.

(51) Int. Cl.[7] ................................. A61M 1/12
(52) U.S. Cl. .................. 600/17; 600/439; 600/587; 623/3.28
(58) Field of Search ............... 600/17, 16, 507, 600/587, 407, 438, 439, 459, 449, 450, 465; 623/3.1, 3.28, 3.13

(56) References Cited

U.S. PATENT DOCUMENTS

| | | | |
|---|---|---|---|
| 3,831,203 A | * 8/1974 | Ridgway | 417/383 |
| 4,135,253 A | 1/1979 | Reich et al. | 3/1.7 |
| 4,403,911 A | 9/1983 | Possell | 415/90 |
| 4,598,697 A | * 7/1986 | Numazawa et al. | 600/17 |
| 4,688,998 A | 8/1987 | Olsen et al. | 417/356 |
| 4,704,121 A | 11/1987 | Moise | 623/3 |
| 4,763,032 A | 8/1988 | Bramm et al. | 310/90.5 |
| 4,779,614 A | 10/1988 | Moise | 600/16 |
| 4,846,152 A | 7/1989 | Wampler et al. | 600/16 |
| 4,925,443 A | 5/1990 | Heilman et al. | 600/16 |
| 4,927,407 A | 5/1990 | Dorman | 600/16 |
| 4,944,722 A | 7/1990 | Carriker et al. | 600/16 |
| 4,957,504 A | 9/1990 | Chardack | 623/3 |
| 4,993,427 A | * 2/1991 | Barr et al. | 600/453 |
| 5,006,111 A | * 4/1991 | Inokuchi et al. | 600/17 |
| 5,049,134 A | 9/1991 | Golding et al. | 604/151 |
| 5,324,177 A | 6/1994 | Golding et al. | 417/423.1 |
| 5,326,344 A | 7/1994 | Bramm et al. | 623/3 |
| 5,385,581 A | 1/1995 | Bramm et al. | 600/16 |
| 5,388,583 A | 2/1995 | Ragauskas et al. | 600/438 |
| 5,469,006 A | 11/1995 | Pinkerton | 310/90.5 |

FOREIGN PATENT DOCUMENTS

| | | |
|---|---|---|
| DE | 41 23 433 A1 | 2/1992 |
| WO | WO 97/49440 | 12/1997 |

* cited by examiner

*Primary Examiner*—Kennedy Schaetzle
(74) *Attorney, Agent, or Firm*—Buchanan Ingersoll, P.C.

(57) ABSTRACT

A flow rate control method and apparatus for a blood pump is provided wherein multiple sensors are utilized to measure physical dimensions of a ventricle to calculate either a cross sectional area or a volume of the ventricle during distention and contraction. The multiple sensors are positioned at spaced locations around the ventricle, and may be attached to or imbedded in the ventricle. The sensors may be in the same plane for determining a cross sectional area or in different planes for determining a volume. The area or volume is generally proportional to a corresponding area or volume of the ventricle such that the calculated area or volume is indicative of distention and contraction of the volume. The area or volume is utilized to control the blood pump flow rate to avoid overly distending or contracting the ventricle and for operating the flow rate in a pulsatile manner to closely approximate the natural pumping action of the heart.

10 Claims, 11 Drawing Sheets

BLOOD PUMP FLOW RATE CONTROL METHOD AND APPARATUS UTILIZING MULTIPLE SENSORS

CROSS REFERENCE TO RELATED APPLICATION

This application is a continuation-in-part of U.S. patent application Ser. No. 09/273,384, filed Mar. 22, 1999, and allowed on Nov. 7, 2001, which is a divisional application of U.S. patent application Ser. No. 08/978,670, filed Nov. 26, 1997, now U.S. Pat. No. 5,928,131.

BACKGROUND

1. Field of the Invention

The present invention relates generally to rotary pumps utilized to pump blood, and more particularly to a flow rate control method and apparatus utilizing multiple sensors for use in determining and area or volume of a heart ventricle during natural distention and contraction and utilizing that information to control the flow rate of a blood pump.

2. Description of the Prior Art

The use of rotary pumps (i.e. axial, centrifugal, mixed flow) to pump fluids and in particular blood is well known by those skilled in the art. A rotary pump, in general, consists of an outer housing, with inlet and outlet ports, and an impeller mounted on a shaft (with mechanical bearings and seals) within the outer housing for rotation about an axis. Mechanical bearings are susceptible to wear and premature failure and can generate sufficient heat and mechanical stresses to cause unacceptable blood damage. Shaft seals are also susceptible to wear and heat generation, which can lead to leakage, blood clot formation, bearing seizure, and bacterial growth. Examples of rotary pumps utilizing shaft mounted impellers with bearings and seals are disclosed in Reich et. al. U.S. Pat. No. 4,135,253; Possell U.S. Pat. No. 4,403,911; Moise U.S. Pat. No. 4,704,121; and Dorman U.S. Pat. No. 4,927,407.

Numerous pumps have been designed to circumvent the above problems by employing a lubricant flush of rotary pump mechanical bearings. Examples of such pumps are disclosed in Carriker et al. U.S. Pat. No. 4,944,722 and Wampler et al. U.S. Pat. No. 4,846,152. These types of pumps can have several problems including not having the ability to be fully implantable due to the need for a percutaneous supply line and external reservoir to achieve bearing flushing. Also the potential for infection and leakage exists due to the flushing fluid and percutaneous lines. In addition the mechanical bearings can still require replacement after time because they directly contact other pump structures during operation.

By employing a rotary fluid pump with a magnetically suspended impeller, all of the above mentioned problems can be avoided. Examples of such pumps are disclosed in Bramm et al. U.S. Pat. No. 5,326,344; Olsen et al. U.S. Pat. No. 4,688,998 and Moise U.S. Pat. No. 4,779,614. A problem which can be associated with all of the cited inventions is that a single gap is employed for both the blood flow pathway through the pump and for the magnetic suspension and rotation of the impeller. These two functions have directly opposing requirements on the size of the gap. As a blood flow pathway, the gap should be large to avoid blood damage. As a magnetic suspension and rotation gap, the gap should be small to minimize the size of the magnetic suspension and rotation components and also to allow for efficient use of energy to achieve impeller suspension and rotation. Consequently, for these types of pumps, any gap size selected can result in an undesirable compromise between blood damage, device size, and energy requirements.

Examples of pumps having separate gaps for primary blood flow and impeller rotation are disclosed in Golding et al. U.S. Pat. No. 5,324,177 and Golding et al. U.S. Pat. No. 5,049,134. However, these pumps also use the rotation gap to implement hydrodynamic suspension bearings for the rotor. Such hydrodynamic bearings can subject the blood to excessive shear stresses which can unacceptably damage the fragile components of the blood. Additionally, the Golding et. al. pumps place the stationary magnetic components inside a center-bore of a rotating assembly. Such configurations generally cause the mass and rotational inertia of the rotating assembly to be larger than those in a system in which the stationary magnetic components are placed around the outer surface of the rotating assembly. Rotating assemblies having large masses and rotational inertias can be undesirable because the axial and radial bearing elements must be made relatively large in order to maintain proper alignment of the rotating assembly during shock, vibration, and acceleration.

The flow rate of blood pumps that are capable of creating negative inlet pressures must be dynamically adjusted to match the blood flow rate into the ventricle of the heart, typically the left ventricle. If too little flow is produced by the blood pump, the tissues and organs of the body may be inadequately perfused, and the blood pressure in the left ventricle will increase—potentially causing excessive pulmonary pressure and congestion. Conversely, if the flow rate of the blood pump is too high, excessive negative pressure may be created in the left ventricle and in the inlet to the pump. Excessive negative blood pressure is undesirable for the following reasons: 1) Unacceptable levels of blood damage may be caused by cavitation; 2) The pump may be damaged by cavitation; 3) The walls of the ventricle may collapse and be damaged; and 4) The walls of the ventricle may collapse and block the blood flow pathway to the pump.

By employing a control system to dynamically control the flow rate of the pump to avoid excessive negative blood pressure the above mentioned problems can be avoided. One example of such a control system is disclosed in Bramm et al., U.S. Pat. No. 5,326,344. Bramm describes a method of dynamically controlling the flow rate of a pump based on a signal derived from a single pressure sensor located within the pump inlet. One problem which can be associated with such a pressure sensing system is the difficulty in achieving long-term stability of such a sensor, particularly in light of the relatively low pressures (0 to 20 mm Hg) that must be resolved and the hostile environment in which the sensor is operated. Another problem which can be associated with such a pressure sensing system is that the effect of changing atmospheric pressure can cause inaccurate sensing of the pressure needed to properly control the pump.

Many patients that are in need of cardiac assistance due to their heart's inability to provide adequate blood flow are also predisposed to cardiac arrhythmias. Such arrhythmias can adversely affect blood flow when a cardiac assist device is used, particularly when only uni-ventricular cardiac assistance is being provided. By combining an arrhythmia control system with a cardiac assistance system, the above mentioned problems can be alleviated. One example of such a combined cardiac assist and arrhythmia control system is disclosed by Heilman et al. U.S. Pat. No. 4,925,443. Heilman describes a cardiac assist device that directly compresses the myocardium to achieve increased blood flow combined with an arrhythmia control system. Some problems which can be associated with direct compression of the myocardium can include difficulty in conforming to a wide range of heart shapes and sizes, difficulty in adequately attaching such a device to the heart, and damage of the myocardium due to compression and abrasion.

Accordingly, there is a need for a blood pump which overcomes the aforementioned problems that can be associated with conventional blood pumps and also a system of dynamically controlling such a blood pump to avoid the previously described problems that can occur with control systems using pressure sensors. Moreover, such blood pump and control system should be able to cooperate with an arrhythmia control system for improved cardiac arrhythmia treatment.

SUMMARY

A flow rate control method and apparatus for use with a blood pump is provided wherein multiple sensors can be employed to sense physical dimensions of a heart ventricle to calculate either a cross sectional area or a volume of the ventricle during distention and contraction. The multiple sensors can be positioned at selected locations around the ventricle, and may be attached to or imbedded in the ventricle. The sensors can be ultrasonic transducers positions at selected points around the left ventricle for obtaining measurements to approximate a cross sectional area of the ventricle. Each of the sensors can be positioned in a plane through the ventricle where the physical characteristic to be determined is a cross sectional area. Where the physical characteristic to be determined is a volume, the sensors can be positioned in different planes. In either case, the area or volume is generally proportional to a corresponding area or volume of the ventricle such that the calculated area or volume is indicative of distention and contraction of the volume. The calculated area or volume can be a more precise indication of distention and contraction than a single radial dimension measurement. The area or volume can be utilized to control the blood pump flow rate to avoid overly distending or contracting the ventricle and for operating the flow rate in a pulsatile manner to closely approximate the natural pumping action of the heart.

Although any type of suitably controllable blood pump could be controlled using the method and apparatus described above, the blood pump apparatus can preferably include a stator member containing a magnetically suspended and rotated rotor member. The rotor can preferably be magnetically suspended within the stator both radially and axially. The blood pump can also have an associated magnetic suspension control system, a blood pump flow rate control system, and an arrhythmia control system. The blood pump can preferably be a centrifugal pump wherein an impeller draws blood from the left ventricle of a the heart and delivers it to the aorta thereby reducing the pressure that must be generated by the left ventricle. The blood pump can also be of a relatively small size such that it can be completely implanted within the human body. If bi-ventricular cardiac assist is needed a second such blood pump can be implanted to assist the right ventricle. The impeller of the centrifugal pump can be an integral part of a rotor assembly. The rotor assembly can preferably be suspended by permanent magnet radial bearings and a Lorentz-force axial bearing. The Lorentz-force axial bearing can generate bi-directional axial forces in response to an applied current. The blood pump can also include an axial position sensor and an axial position controller. The axial position sensor can monitor the axial position of the rotor and provide feedback to the controller to maintain the axial position of the rotor. The axial position controller can also adjust the axial position of the rotor such that steady-state axial loads due to gravity, acceleration or the centrifugal pump impeller are offset by the inherent axial forces generated by the permanent magnet radial bearings. By offsetting the steady-state axial forces using the axial position controller, the power required by the Lorentz-force axial bearing is minimized. The rotor assembly can be rotated by an electric motor.

A primary blood flow inlet path can preferably be through a relatively large center bore provided in the rotor. A secondary blood flow inlet path can be through an annular gap which is formed between the rotor and the stator of the pump as a result of the radial magnetic suspension. In order to minimize the size of the device, all of the magnetic suspension and rotation forces can be applied across the relatively small annular gap. All blood contacting surfaces of the pump are continuously washed to avoid blood clots and protein deposition.

The speed of the centrifugal pump can be dynamically controlled to avoid excessive negative pressure in the left ventricle using the multiple sensor control method and apparatus described above. An alternative blood pump flow rate control system can utilize an electronic heart caliper operatively attached to the outside surface of the heart to provide feedback to the blood pump flow rate control system. The heart caliper generally measures a single, generally radial dimension of the ventricle which is indicative of distention and contraction of the ventricle.

The blood pump flow rate control system can preferably operate in two modes, continuous and pulsatile. In the continuous mode of operation, the pump speed can be controlled to hold the sensed or calculated left ventricle dimension, area or volume at a defined setpoint. In the pulsatile mode of operation, the pump speed can be dynamically adjusted to cause the sensed or calculated left ventricle dimension, area or volume to alternate between two predefined setpoints.

The blood pump can also be utilized to improve the functioning of an arrhythmia control system. Electrodes placed in or on the surface of the heart combined with an associated arrhythmia control system can be provided to detect and treat cardiac arrhythmias including bradycardia, tachycardia, and fibrillation. In order to reduce the energy needed for the arrhythmia control system to treat fibrillation, the blood pump flow rate control system can be employed to purposely reduce the radial dimension of the ventricle prior to delivering a defibrillation pulse. By minimizing the amount of blood within the ventricle chamber (a direct result of reducing the radial dimension thereof), a larger fraction of the defibrillation energy supplied by the arrhythmia control system is delivered to the myocardium, where it is needed, and a smaller fraction of the energy is delivered to the blood, where it is unnecessary.

Other details, objects, and advantages of the invention will become apparent from the following detailed description and the accompanying drawing figures of certain presently preferred embodiments thereof.

BRIEF DESCRIPTION OF THE DRAWINGS

A more complete understanding of the invention can be obtained by considering the following detailed description in conjunction with the accompanying drawings, wherein.

DETAILED DESCRIPTION OF THE PREFERRED EMBODIMENTS

Figure 1:
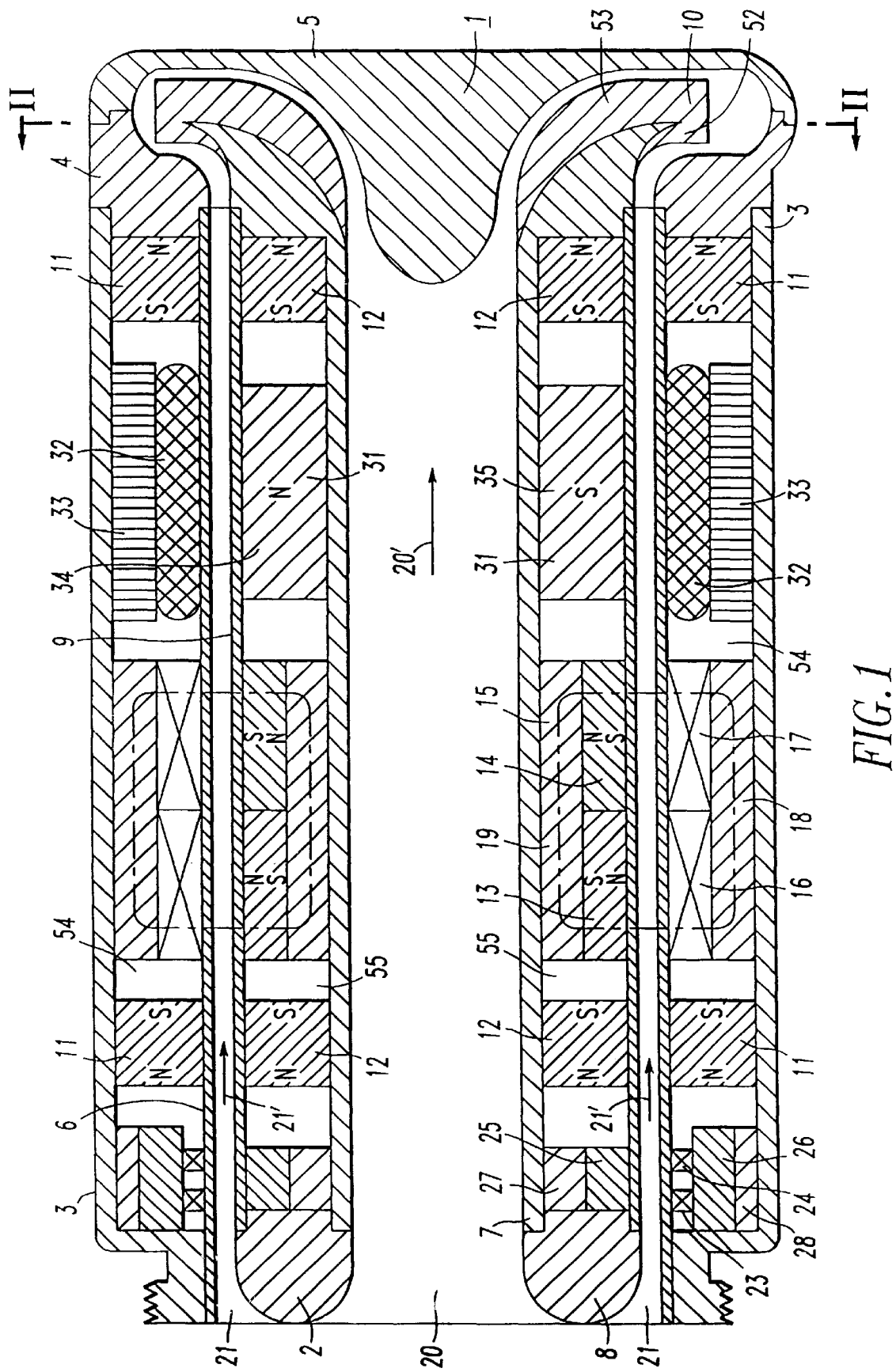
FIG. 1 is a cross section view of an embodiment of the blood pump having a magnetically suspended and rotated rotor assembly.

Referring now to the drawing figures wherein like reference numbers refer to similar parts throughout the several views, a presently preferred blood pump apparatus is shown in FIG. 1 having a stator assembly 1 and a rotor assembly 2.

The stator assembly 1 can have an outer stator shell 3, an inner volute housing 4, an outer volute housing 5, and a thin-walled stator liner 6. The stator shell 3, inner volute housing 4 and stator liner 6 can each be made from titanium. The stator liner 6 can have a thickness from about 0.005 to 0.015 inch, and preferably is about 0.010 inch. The outer stator shell 3, an inner volute housing 4, and stator liner 6 can preferably be welded together to form a hermetically sealed annular stator chamber 54. The stationary magnetic suspension and motor components can be advantageously housed in the stator chamber 54.

The rotor assembly 2 can have a relatively large center bore 228 which can be the primary blood flow path 22 through the pump. Preferably the center bore 228 is about 0.50 inch. The rotor assembly 2 can include an inner rotor support sleeve 7, a rotor end cap 8 and a thin-walled rotor liner 9. The inner rotor support sleeve 7, rotor end cap 8 and rotor liner 9 can each be made from titanium. The rotor liner 9 can have a thickness from about 0.005 to 0.015 inch and can preferably be about 0.010 inch. The rotor support sleeve 7, rotor end cap 8 and rotor liner can preferably be welded together to form a hermetically sealed annular rotor chamber 55. The rotating magnetic suspension and motor components can be advantageously housed in the rotor chamber 55. The inner rotor support sleeve 7 can be fabricated with an integral impeller 10 or, alternately, the impeller 10 can be fabricated independently then welded or bonded to the rotor support sleeve 7.

The blood contacting surfaces of the blood pump can be coated with a diamond-like carbon film or a ceramic film. Such films enhance the long term bio-compatibility of the surfaces by improving their surface finish and abrasion resistance. Companies capable of providing such films include Diamonex Performance Products, Allentown, Pa, and Implant Sciences Corporation, Wakefield, Mass.

The primary inlet blood flow path 20, can be through the center bore 208 of the inner rotor support sleeve 7. A secondary inlet blood flow path 21, can be through the annular gap 218 which is the radial magnetic suspension gap between the stator liner 6 and the rotor liner 7. The annular gap 218 can preferably be about 0.020 inch. The blades of the impeller 10 can include outer portions 52, that purposely draw blood through the secondary inlet blood flow path 21, and inner portions 53, that purposely draw blood through the primary inlet blood flow path 20.

When polarized as indicated in FIG. 1, radial magnetic repulsion forces are generated between permanent magnets 11, mounted in the stator chamber 54, and permanent magnets 12, mounted in the rotor chamber 55. As the rotor assembly 2, is moved radially downward relative to the stator assembly 1, the repulsion force between the lower portion 29, of permanent magnets 11 and 12 increases while the repulsion force between the upper portion 30, of permanent magnets 11 and 12 decreases. A net upward force is thus created which tends to restore the rotor assembly 2, to a radially aligned position. Likewise, as the rotor assembly 2, is moved radially upward relative to the stator assembly 1, the repulsion force between the upper portion 30, of permanent magnets 11 and 12 increases while the repulsion force between the lower portion 29, of permanent magnets 11 and 12 decreases. A net downward force is thus created that tends to restore the rotor assembly 2 to the radially aligned position. The described radial repulsion forces tend to cause the rotor assembly 2 to remain radially suspended with respect to the stator assembly 1. Permanent magnets 11 and 12 can preferably be fabricated of magnetically hard material having a relatively high energy product such as Neodymium Iron Boron.

An assembly of permanent magnets 13, 14, coils 16, 17, and back irons 15, 18 cooperate to form a Lorentz-force actuator which can be employed as an axial bearing to support the rotor assembly 2 axially. Permanent magnets 13 and 14 cause magnetic flux 19, to flow radially from the outer surface of magnet 13, radially across the secondary blood flow path 21, radially through coil 16, axially through the stationary actuator back-iron 18, radially through coil 17, radially across the secondary blood flow path 21, radially through magnet 14, axially through the rotating actuator back-iron 15, and radially through magnet 13. Permanent magnets 13 and 14 can preferably be fabricated of a magnetically hard material having a relatively high maximum energy product such as Neodymium Iron Boron and can preferably be bonded to the rotating actuator back-iron 15, which in turn can preferably be bonded to the inner rotor support sleeve 7. The stationary actuator back-iron 18, and rotating actuator back-iron 15, can preferably be fabricated of a soft magnetic material having a high saturation flux density. One such material is 48% Iron-48% Cobalt-2% Vanadium available as HIPERCO® 50A from Carpenter Technology Corporation, Reading Pa. Coils 16 and 17 can be fabricated from copper or silver wire and can preferably be bonded to the stationary actuator back-iron 18, which in turn can be bonded to the outer stator shell 3. When coils 16 and 17 are energizing such that current flows in a clockwise direction in coil 16 and in a counterclockwise direction in coil 17, as viewed from the pump inlet 22, a net axial Lorentz force is generated which tends to move the rotor assembly 2 to the right. If the direction of the currents in coils 16 and 17 is reversed such that current flows in a counterclockwise direction in coil 16 and in a clockwise direction in coil 17, as viewed from the pump inlet 22, a net axial Lorentz force is generated which tends to move the rotor assembly 2, in the left. A Lorentz-force actuator as described can be preferable to attractive ferromagnetic actuators because: a single Lorentz-force actuator is capable of producing bi-directional forces; the force output is a linear function of input current; the bandwidth is wider; the attractive radial force between the moving and stationary portions of the actuator is relatively low; and the generated force is parallel to the axial gap formed between the moving and stationary portions of the actuator.

A permanent magnet 31, armature windings 32 and back-iron 33 cooperate to form a slotless, brushless DC motor with a coreless armature. Such slotless, coreless motors are well understood by those skilled in the art and are described in U.S. Pat. No. 4,130,769. A 2-pole permanent magnet ring 31 causes magnetic flux to flow radially from the its north pole 34, across the secondary blood flow gap 21, radially through the armature windings 32, circumferentially through the stator back-iron 33, radially through the armature windings 32, radially across the secondary blood flow gap 21 to the south pole 35 of the permanent magnet ring 31. Interaction between axial current flowing in the armature windings 32 and the radial magnetic flux produces torque between the rotor assembly 2 and the stator assembly 1. The permanent magnet ring 31 can preferably be fabricated of a magnetically hard material having a relatively high maximum energy product such as Neodymium Iron Boron. Alternatively, the permanent magnet ring 31 can be replaced with permanent magnet ring assemblies having more than 2 poles in order to reduce the size and/or increase the efficiency of the motor. The stator back-iron assembly 33, can be fabricated from a stack of magnetically soft lamination rings preferably having high resistivity and a high saturation flux density. One such material is 48% Iron-48% Cobalt2% Vanadium and is available as HIPERCO® 50A from Carpenter Technology Corporation, Reading Pa. Electrically insulated laminations are used in the stator back-iron assembly 33 to minimize power losses caused by eddy currents which are induced by the rotating magnetic field produced by permanent magnet ring 31. It is understood that a conventional salient-pole brushless DC motor could be used in place of the described motor, however, a slotless, coreless, motor can be preferable because cogging torque can be eliminated in slotless motors allowing smoother, quieter operation as compared to salient-pole brushless DC motors, and slotless, coreless, motors generally have larger radial gaps between the permanent magnets in the rotor and the stator back-iron resulting in lower attractive radial forces. Attractive radial forces generated by the motor can be undesirable since they tend to oppose the repulsive radial suspension forces generated by the permanent magnet radial bearing magnets resulting in reduced radial suspension stiffness. Such slotless, brushless, coreless DC motors are available from companies such as Electric Indicator Company, Inc. Norwalk, Conn.; Portescap U.S., Inc., Hauppauge, N.Y.; Maxon Precision Motors, Inc., Fall River, Mass.; and MicroMo Electronics, Inc., Clearwater, Fla.

An assembly of coils 23, 24 and ferromagnetic rings 25, 26 cooperate to form an axial position sensor which is used to monitor the axial position of the rotor assembly 2 with respect to the stator assembly 1. The two coils 23, 24 can be fabricated from copper wire. A first ferromagnetic ring 25 causes the inductance of a first coil 23 to increase and the inductance of the second coil 24 to decrease as it is moved to the left. Likewise, the inductance of the first coil 23 decreases and the inductance of the second coil 24 increases as the first ferromagnetic ring 25 is moved to the right. A second ferromagnetic ring 26 can serve to both magnetically shield and increase the Q of the coils 23, 24. The two ferromagnetic rings 25, 26 can preferable be made of a ferrite material having a high permeability at the excitation frequency of the coils 23, 24. One such material is MATERIAL-W® available from Magnetics, Division of Spang & Co., Butler, Pa. A pair of spacers 27, 28 can be used to radially locate the two ferromagnetic rings 25, 26.

Figure 2:
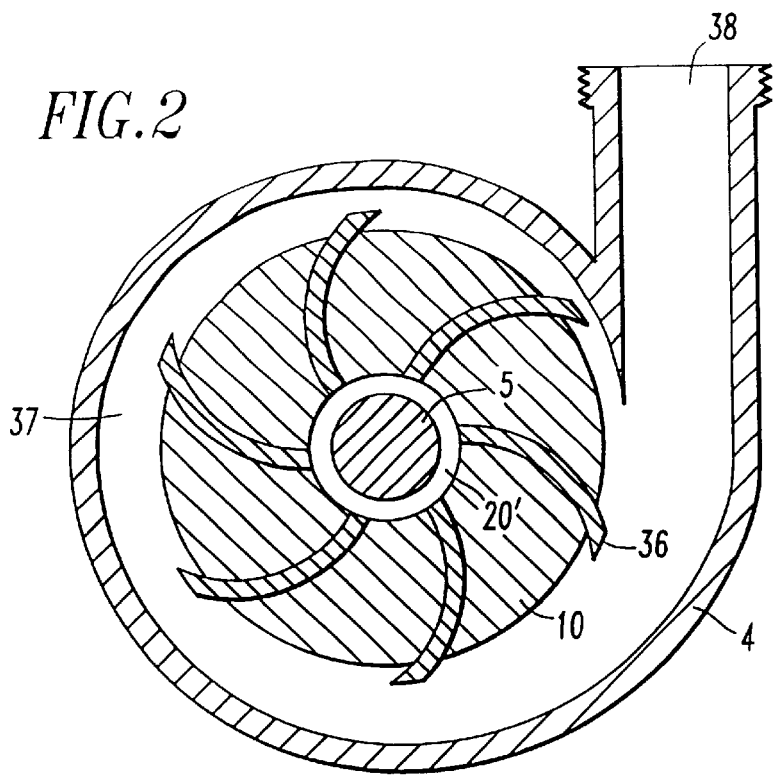
FIG. 2 is a view of the blood pump in FIG. 1 taken along line II—II.

An annular pump chamber having a single volute passage, is shown in FIG. 2. The annular pump chamber is shown having an outer volute housing 5 and an inner volute housing 4. The impeller 10 rotates within the pump chamber about a projection of the outer volute housing 5 and within the inner volute housing 4. A series of impeller blades 36 propel blood from the primary blood flow path 20, centrifugally around the volute passage 37, and out the outflow port 38.

Figure 3:
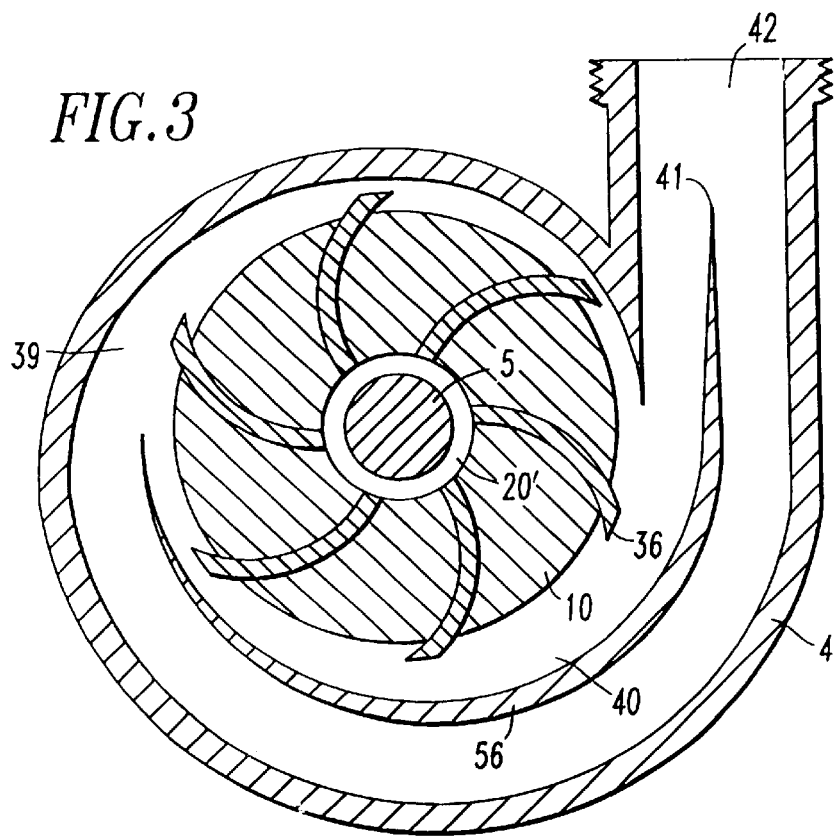
FIG. 3 is a view of the blood pump shown in FIG. 2 having a double-volute configuration.

The single-volute centrifugal pump illustrated in FIG. 2 inherently develops a radial force on the impeller which must be offset by the permanent magnet radial bearings 11, 12, shown in FIG. 1. To minimize this radial force, an alternative, double volute, configuration, as shown in FIG. 3, can be employed. A double volute passage can be formed in the annular pump chamber by interposing a septum 56 in the single volute passage 37 (shown in FIG. 2) to form a pair of volute passages 39, 40 which are radially opposed. It is to be understood that the overall size of the double volute passages and outlet 42 may be larger than single volute passage 37 and outlet 41 to accommodate the septum 56 and allow for adequate blood flow through the annular pump chamber. The radially-opposed volutes 39, 40 produce opposing impeller forces that balance one another and thus minimize the radial force that must be offset by the permanent magnet radial bearings 11, 12. In the double volute configuration, similarly to the single volute design, the impeller 10 rotates about a projection of the outer volute housing 5 and within the inner volute housing 4. However, the impeller blades 36 now propel blood from the primary blood flow path 20 through both centrifugal volute passages 39, 40. The blood, flowing separately in each volute passage 39, 40, combines at confluence point 41 and is delivered to the outlet 42. It should be understood that other impeller-volute arrangements could be derived by those skilled in the art and the invention is not to be limited to the particular configurations illustrated and described herein.

Figure 4:
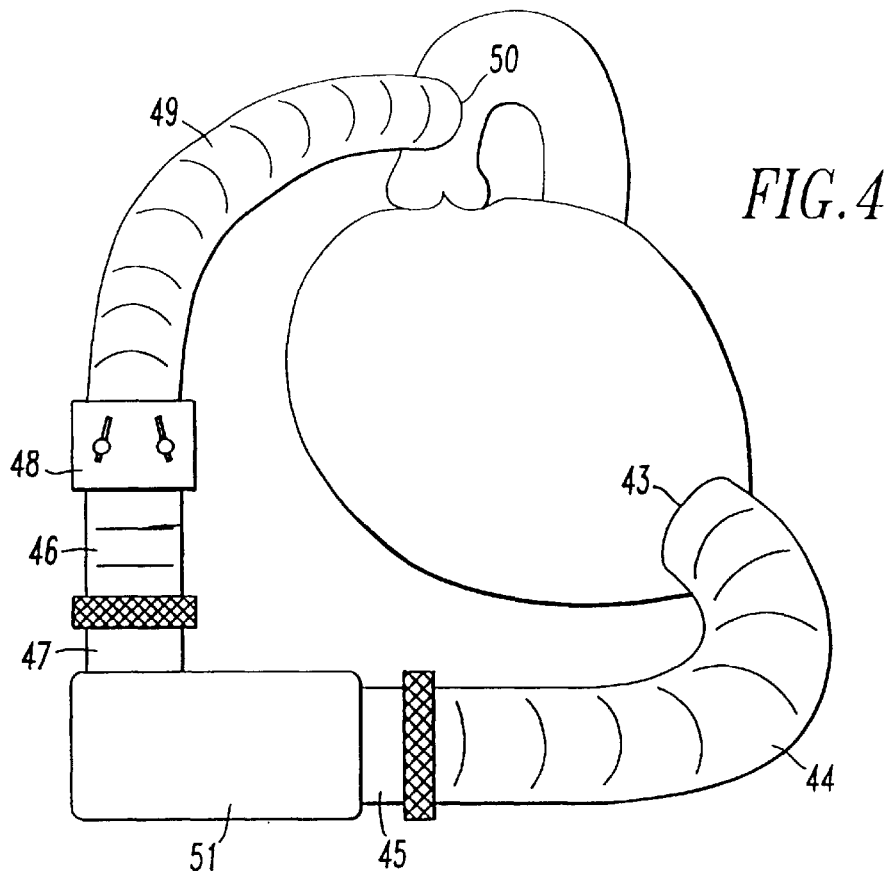
FIG. 4 is a perspective view of the blood pump of FIG. 1 connected to a circulatory system.

Referring now to FIG. 4, one method of connecting of the blood pump 51 to the circulatory system is schematically illustrated. Several cannulas 44, 46, 49 can be provided to connect the pump 51 between the left ventricle of the heart and the aorta. A hole is cored in the apex of the left ventricle at location 43 and one cannula 44 directs blood from the left ventricular cavity to the pump inlet 45. Another cannula 46 directs blood from the pump outlet 47 to an in-line artificial heart valve assembly 48. Alternatively, a solenoid actuated valve could be used in place of valve assembly 48. The artificial heart valve assembly 48 can preferably be provided to prevent retrograde blood flow from the aorta, through the pump, and into the left ventricle in the event of a failure of the blood pump or an associated control system. From the outlet of the heart valve assembly 48, another cannula 49 directs the blood to the ascending aorta 50. For bi-ventricular cardiac assist, a second pump could be connected in like fashion between the right ventricle and pulmonary artery.

Figure 5:
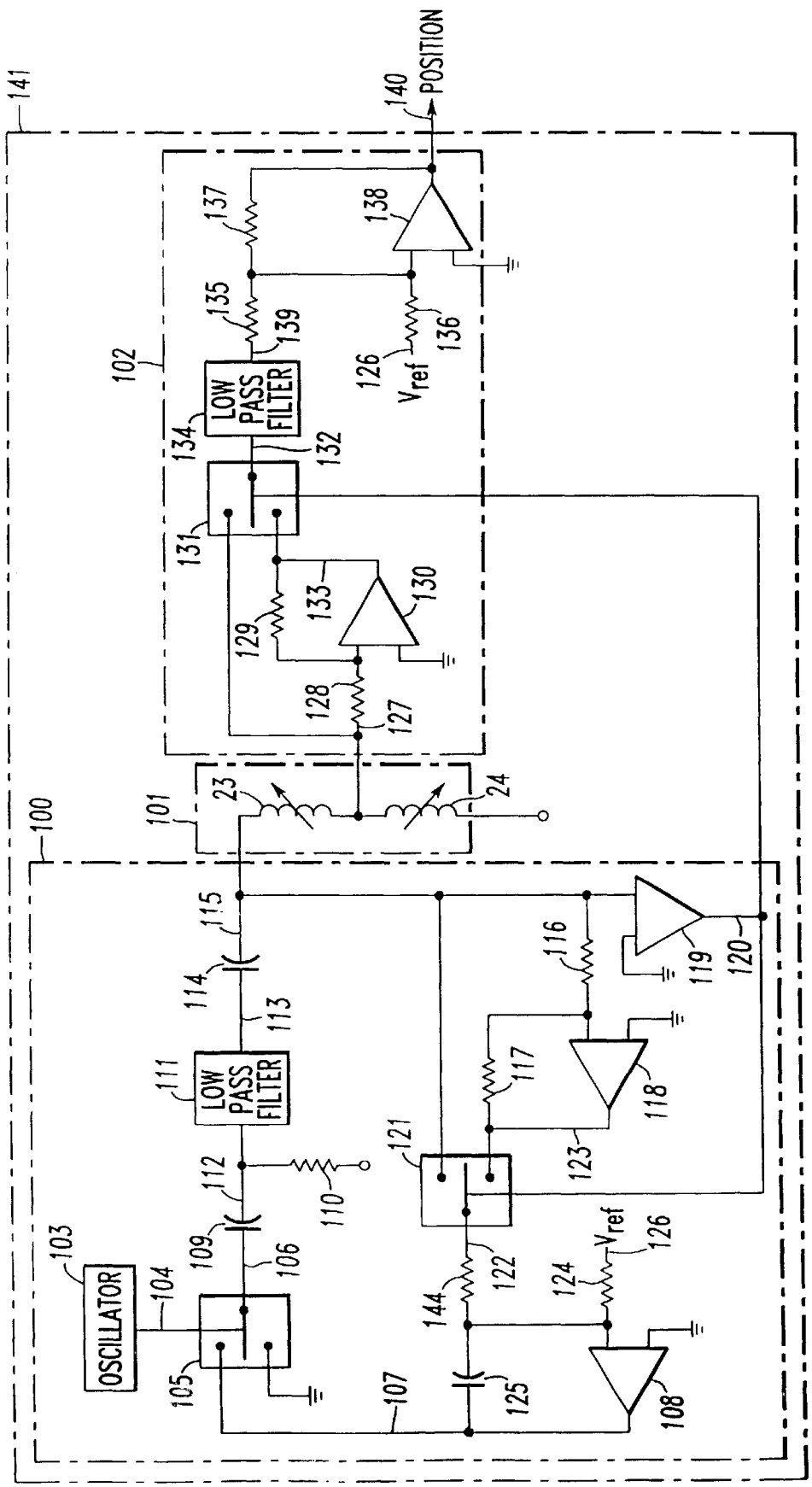
FIG. 5 is a schematic diagram of a circuit for sensing the axial position of the magnetically suspended rotor assembly.

An axial position sense subsystem 141 can have the circuitry shown in FIG. 5. The subsystem 141 can utilize the ratio of the inductances of coils 23 and 24 to measure the axial position of the rotor assembly 2. The subsystem 141 can include an amplitude-stabilized sine-wave oscillator 100, which is used to excite coils 23 and 24 arranged as a half-bridge 101, and a synchronous demodulator 102. Synchronous demodulation is used to detect the relatively low amplitude signals output from the half-bridge circuit 101 because the synchronous demodulation technique effectively filters electrical noise at all frequencies except those centered about the excitation frequency. An oscillator 103 generates a square wave output 104, which is used to control analog switch 105. The output 106, of analog switch 105 is a square wave that alternates between the output voltage 107, of operational amplifier 108, and ground. A capacitor 109 and a resistor 110 form a highpass filter that removes the DC offset from signal 106. A lowpass filter 111 attenuates the upper harmonics of input signal 112 resulting in a sine-wave output signal 113. The lowpass filter 111 is of sufficient order and type to attenuate the third harmonic of the square wave input 112 by 40 dB or more. One possible configuration for low pass filter 111 is a $5^{th}$ order Butterworth type. A capacitor 114 removes any DC offset from the output 113 of the lowpass filter 111. An AC sine-wave 115 is used to excite the half-bridge network 101. A pair of resistors 116, 117 and operational amplifier 1 18 form an inverting circuit with a gain of−1. A comparator 119 detects the sign of the sine-wave excitation signal 115. The output 120 of the comparator 119 is used to control an analog switch 121. When the sign of sine-wave 115 is negative, the output 122 of the analog switch 121 is connected to the non-inverted sine-wave signal 115. When the sign of sine-wave 115 is positive, the output 122, of the analog switch 121 is connected to the inverted sine-wave signal 123. The output 122 is thus the inverted, full-wave rectified representation of the excitation sine-wave signal 115. An operational amplifier 108, a pair of resistors 123,124 and a capacitor 125 form an integrating difference amplifier. The output 107 of the operational amplifier 108 increases if the average full-wave rectified representation of the excitation sine-wave signal 115 is less than the applied precision reference voltage 126. Likewise the output 107 of the operational amplifier 108 decreases if the average full-wave rectified representation of the excitation sine-wave signal 115 is greater than the applied precision reference voltage 126. Through the described integrating action, the amplitude of the AC signal 106 is controlled as required to maintain the average full-wave rectified representation of the excitation sine-wave signal 115 equal to the applied precision reference voltage 126. As previously described, the ratio of the inductances of coils 23 and 24 is a function of the axial position of the rotor assembly 2 shown in FIG. 1. The amplitude of the output signal 127 of the half bridge circuit 101 formed by coils 23 and 24 thus varies with the axial position of the rotor assembly 2. A pair of resistors 128, 129 and an operational amplifier 130 form an inverting circuit with a gain of −1. The output 120, of the comparator 119 is used to control an analog switch 131. When the sign of sine-wave 115 is negative, the output 132 of the analog switch 131 is connected to the non-inverted output signal 127 of the half bridge circuit 101. When the sign of sine-wave 115 is positive, the output 132 of the analog switch 131 is connected to the inverted output signal 133 of the half bridge circuit 101. The output signal 132 is thus the inverted, full-wave rectified representation of the output signal 127 of the half bridge circuit 101. A lowpass filter 134 attenuates the AC components of the output signal 132. One possible configuration for the low pass filter 134 is an $8^{th}$ order Butterworth type. Several resistors 135, 136, 137, along with an operational amplifier 138 and a precision reference voltage 126 shift and scale the output 139 of the lowpass filter 134 as required for downstream circuits. The output 140 of operational amplifier 138 is thus a representation of the axial position of the rotor assembly 2. Consequently, changes in the output 140 provide a measurement of the axial movement of the rotor assembly 2. The circuit illustrated in FIG. 5 is but one example of a circuit that can be used to detect changes in the ratio of the inductances of coils 23 and 24. It should be understood that other acceptable circuits may be derived by those skilled in the art.

Figure 6:
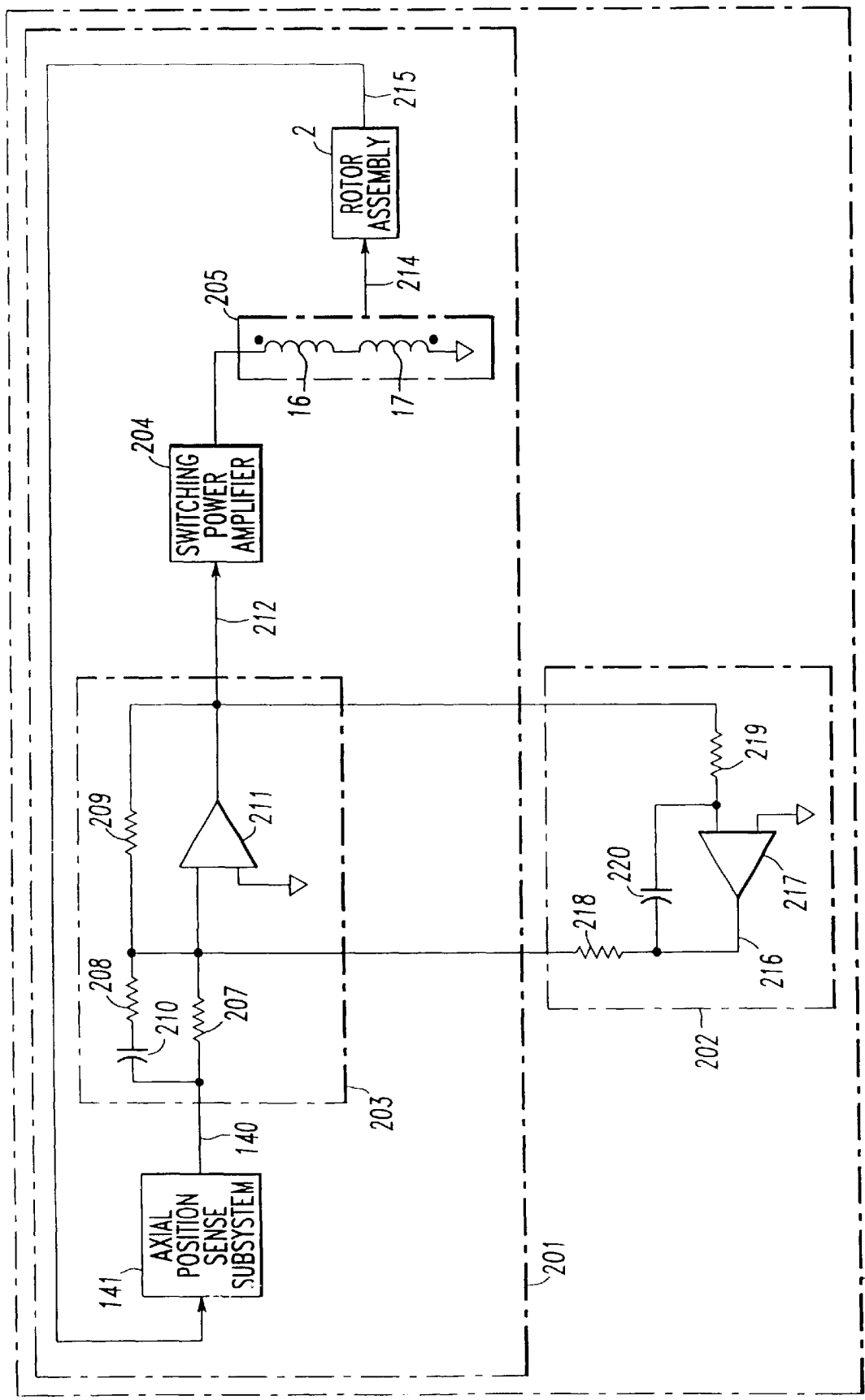
FIG. 6 is a simplified schematic diagram of an axial position controller.

Using the output 140 from the axial position sense subsystem 141, an axial position controller 200, shown in FIG. 6, can be used to both maintain the axial position of the rotor at a defined axial position setpoint and to adjust the axial position setpoint to minimize power dissipation in the Lorentz force actuator. The axial position controller 200 can have the basic circuitry shown in FIG. 6, including circuitry 201, which maintains the rotor at a defined axial position setpoint and circuitry 202, which adjusts the axial position setpoint for minimum power dissipation in the Lorentz-force actuator coils 16, 17. The axial position setpoint maintenance circuit 201, is comprised of the previously described axial position sense subsystem 141, a gain and servo compensation circuit 203, a switching power amplifier 204, the Lorentz-force actuator 205, and the rotor assembly 2. The axial position sense subsystem 141 outputs a signal 140, proportional to the axial position 215 of the rotor assembly 2. Several resistors 207, 208, 209 along with a capacitor 210 and an operational amplifier 211 form a gain and lead compensation network 203, which modifies the gain and phase of signal 140 as required to prevent unstable oscillation of the rotor assembly 2. The design of such gain and lead compensation networks is well understood by those skilled in the art of servo system design. The voltage output 212 of the gain and lead compensation network 203 is input to switching power amplifier 204. Switching power amplifier 204 outputs a current signal 213 that is proportional to the input voltage 212. The design of such transconductance switching amplifiers is well understood by those skilled in the art. The current signal 213 is applied to the coils 16, 17 of the Lorentz-force actuator 205. The Lorentz-force actuator 205 produces an axial force 214 proportional to the applied current signal 213. The axial force 214 is applied to the rotor assembly 2. The axial position 215 of the rotor assembly 2 changes in response to the applied axial force 214. The overall polarity of the described servo loop 201 is such that the force produced by the Lorentz-force actuator opposes displacement of the rotor assembly from the defined setpoint. Those skilled in the art will recognize that the function of the analog, gain and servo compensation circuit 203 can be implemented with software running on a microprocessor or digital signal processor.

Figure 7:
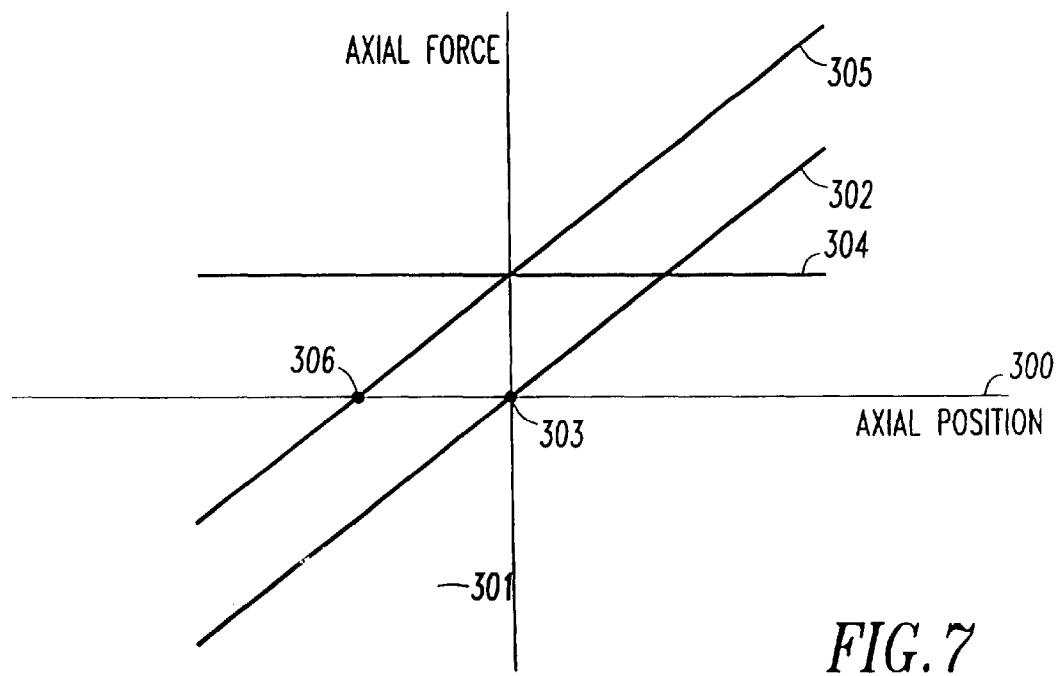
FIG. 7 is a graphical illustration of a minimum power axial position control method.

In FIG. 7, the described minimum axial control power method is illustrated. The x-axis 300 of the graph represents the axial position of the rotor assembly 2 relative to the stator assembly 1, as shown in FIG. 1. The y-axis 301 of the graph represents the axial force applied to the rotor assembly 2. Line 302 represents the inherent axial forces generated by the permanent magnets 11, 12 for small axial displacements of the rotor assembly 2. At point 303 on the graph, the permanent magnets 11, 12 are magnetically aligned and generate no axial force. The slope of curve 302 is dependent on the design of the permanent magnets 11, 12 and may be between 0.2 lb/0.001 inch to 1.0 lb/0.001 inch. Line 304 of FIG. 7 represents a steady-state axial load applied to the rotor assembly 2. The steady-state axial load 304 may be caused by gravity, acceleration, the centrifugal pump impeller, etc. Line 305 of FIG. 7 is the addition of lines 302 and 304 and represents the net force versus axial position of the rotor assembly 2 when the steady-state load 304 is applied. Point 306 defines the axial position of the rotor assembly where the steady-state load force is canceled by the axial force produced by the permanent magnets 11,12. By adjusting the axial position setpoint of the rotor assembly 2 to the axial position defined by point 306, the steady-state actuator force output required to maintain the axial setpoint is zero. Since the power dissipated by the Lorentz-force actuator is proportional to the square of its output force, the net power dissipated by the actuator is minimized when the rotor assembly is operated at the axial position defined by point 306. Likewise, with no steady state load forces applied, the net power dissipated by the actuator is minimized when the rotor assembly is operated at the axial position defined by point 303.

The circuitry 202, shown in FIG. 6, can be employed to effectively adjust the axial setpoint position of the rotor assembly 2 for minimum power dissipation in the Lorentz-force actuator 205 using the previously described method. The steady-state axial position setpoint can be controlled by the voltage output 216 of the operational amplifier 217 and the resistor 218. The circuit formed by the resistor 219, capacitor 220 and the operational amplifier 217 inverts and integrates the voltage output 212 of the gain and lead compensation network 203. Signal 212 is directly proportional to the current flowing in the Lorentz-force actuator coils 16, 17. If the average voltage of signal 212 is positive, indicating that a net positive current is flowing in the actuator coils 16, 17, the output 216 of the operational amplifier 217 decreases and shifts the axial setpoint position of the rotor assembly 2 until the average current flowing in the actuator coils 16, 17 is zero. Likewise, if the average voltage of signal 212 is negative, indicating that a net negative current is flowing in the actuator coils 16,17, the output 216 of the operational amplifier 217 increases and shifts the axial setpoint position of the rotor assembly 2 until the average current flowing in the actuator coils 16,17 is zero. The steady-state axial setpoint position of the rotor assembly 2 is thus adjusted as required for minimum power dissipation in the Lorentz-force actuator 205. Those skilled in the art will recognize that the function of the analog, automatic setpoint adjustment circuitry 202 can be implemented with software running on a microprocessor or digital signal processor.

The flow rate of any blood pump that is capable of creating negative inlet pressures must be dynamically adjusted to match the blood flow rate into the left ventricle. If too little flow is produced by the blood pump, the tissues and organs of the body may be inadequately perfused, and the blood pressure in the left ventricle will increase potentially causing excessive pulmonary pressure and congestion. Conversely, if the flow rate of the blood pump is too high, excessive negative pressure may be created in the left ventricle and in the inlet to the pump. Excessive negative blood pressure is undesirable for the following reasons: 1) Unacceptable levels of blood damage may be caused by cavitation, 2) The pump may be damaged by cavitation, 3) The walls of the ventricle may collapse and be damaged, and 4) The walls of the ventricle may collapse and block the blood flow pathway to the pump. Preferably, the flow rate of the blood pump can be dynamically controlled to avoid these problems.

A pump flow rate controller for the blood pump can be provided to operate the pump such that the flow rate does not overly distend or contract the ventricle. Preferably, a heart measurement apparatus can provide the flow rate controller with information about the dimension of the ventricle during normal distention and contraction. Such a heart measurement apparatus can be an electronic heart caliper, two types of which are illustrated in FIGS. 8a–10b.

Figure 8A:
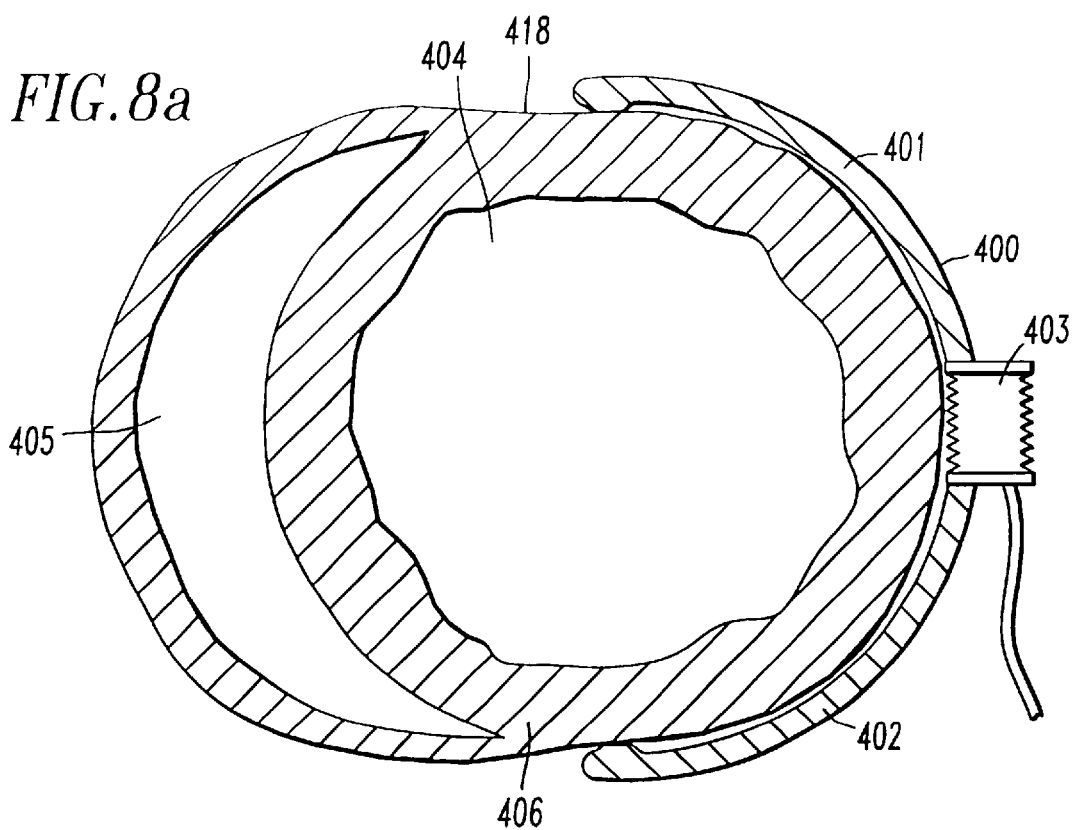
FIG. 8a is a sectional view of a heart caliper attached to a distended ventricle.
Figure 8B:
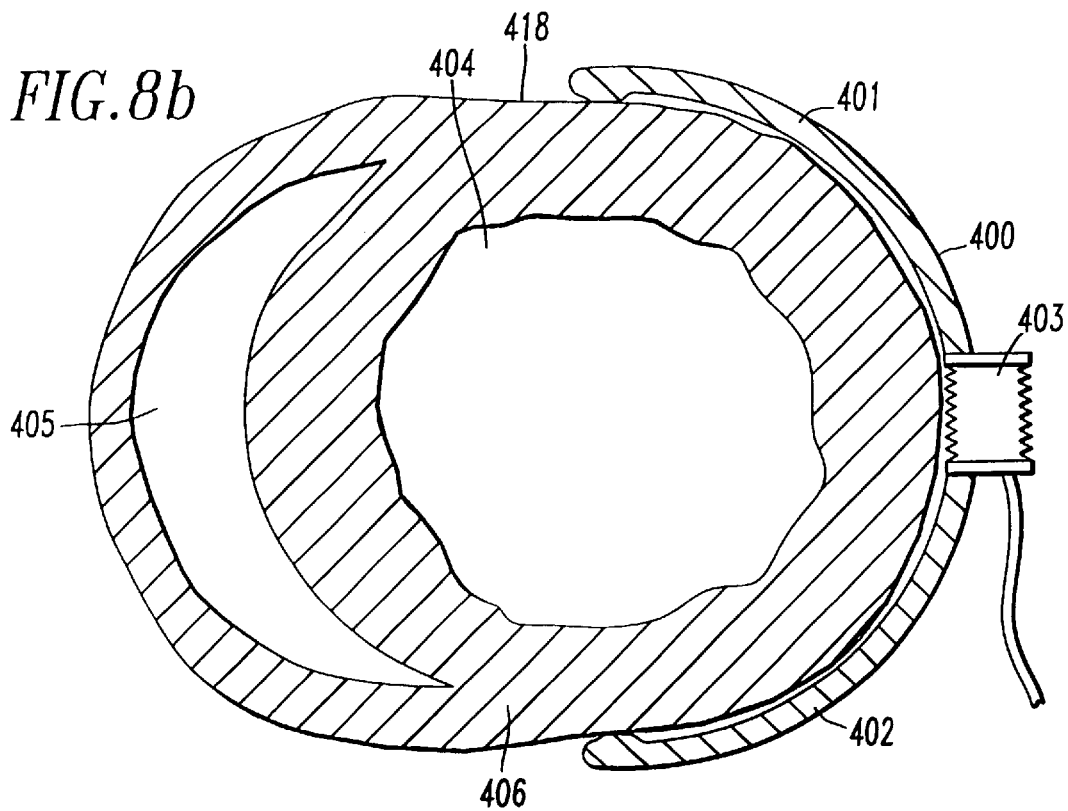
FIG. 8b is a sectional view of a heart caliper attached to a contracted ventricle.
Figure 9:
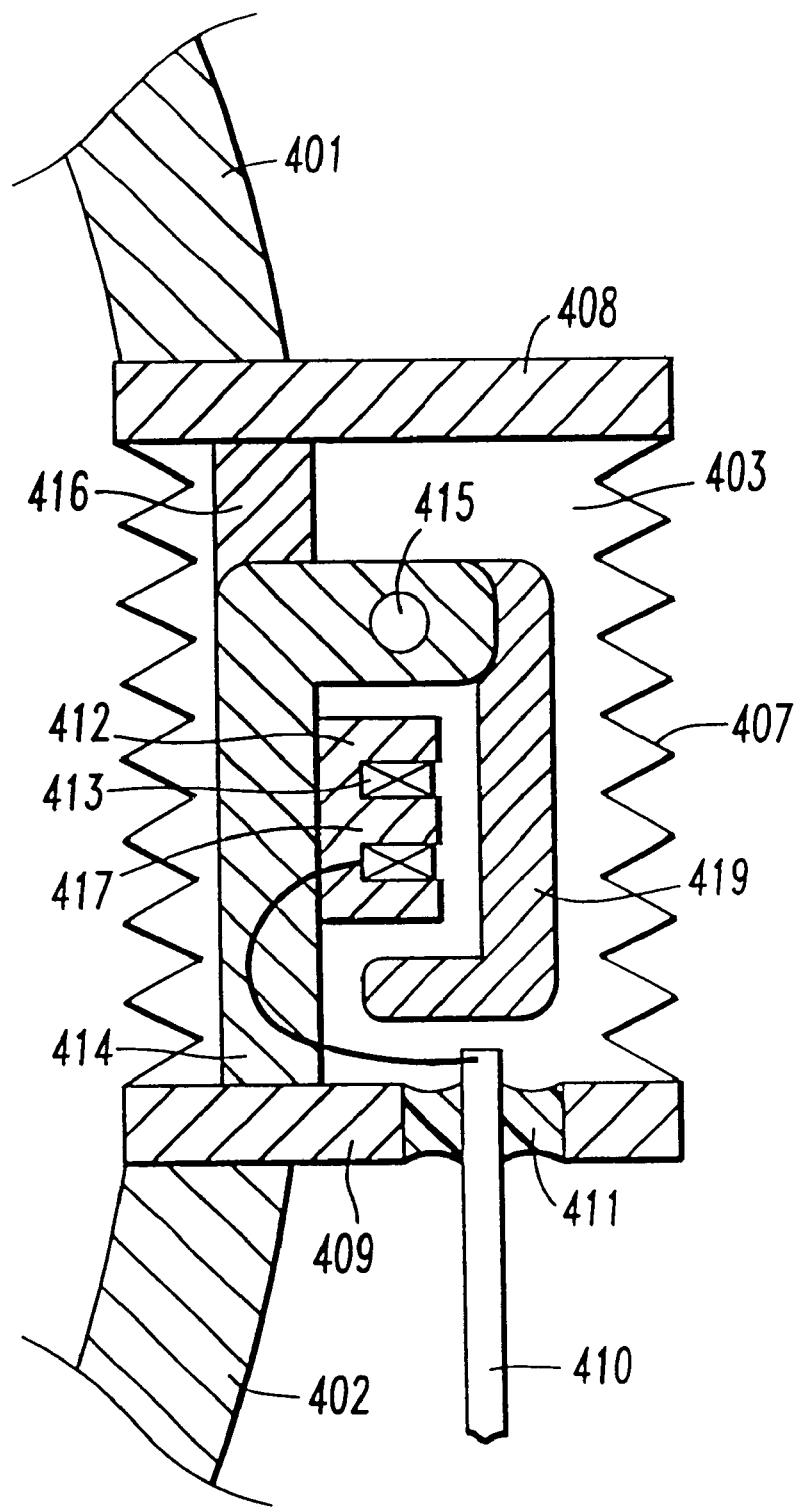
FIG. 9 is an enlarged sectional view of an apparatus for electronically measuring the angle between two caliper arms shown in FIGS. 8a and 8b.

In FIG. 8a, a cross section of a heart is illustrated, including a right ventricle 405 and a left ventricle 404 that is maximally distended by the pressure of the blood contained therein. In FIG. 8b, the left ventricle 404 has been partially depressurized. As blood is withdrawn from the left ventricle 404 the radial dimension of the outside surface 418 of the heart is reduced. By dynamically adjusting the flow rate of the blood pump to avoid excessive distention or contraction of the left ventricle, as indicated by the radial dimension of the exterior surface of the left ventricle, the average blood pump flow rate can be controlled to match the flow rate of blood into the left ventricle. One embodiment of an electronic heart caliper 400 is shown which can be employed to measure the radial dimension of the outside surface 418 of the heart. The heart caliper 400 can include two arms 401, 402 that can be suitably attached to the outside surface 418 of the heart and pivot about a point which can preferably be located inside a hermetically sealed enclosure 403. A measure of the radial dimension of the left ventricle 404 can be achieved by electronically measuring the angle between the caliper arms 401, 402. An angular measurement apparatus which can be used to measure the angle between the caliper arms 401, 402 is illustrated in FIG. 9. The angle measuring apparatus can preferably be contained within a hermetically sealed enclosure 403 in order to protect the internal components from the tissues and fluids of the body. A bellows 407, and end caps 408, 409 can preferably be welded together to form a hermetically sealed chamber. The bellows 407, and end caps 408, 409 are preferably made from titanium. A hermetic electrical feedthrough 410, which can use either a glass or brazed ceramic insulator 411, can be installed in titanium end cap 409. The caliper arms 401, 402 can be effectively connected to a pivot member 415 through respective end caps 408, 409 and respective control arms 414, 416. The caliper arm 401, end cap 408 and control arm 416 can be machined from a single piece of titanium or can be constructed individually and welded or bonded together. Likewise, the caliper arm 402, end cap 409 and control arm 414 can be machined from a single piece of titanium or can be constructed individually and welded or bonded together. A pivot 415 limits the motion of the caliper arms 401, 402 to an arc within a single plane. As the caliper arms 401, 402 move due to distention or contraction of the left ventricle, the extension of control arm 416 moves closer or farther respectively from an eddy-current based position sensor 417 that can be bonded to the control arm 414. The eddy-current based position sensor 417 can be fabricated from a miniature ferrite pot core 412 and a copper coil 413. Such miniature ferrite pot cores are available from Siemens Components, Inc., Iselin, N.J. The eddy-current sensor coil can be connected to two electrical feedthroughs (only one of the two feedthroughs, 410, is shown in FIG. 9). As the metallic control arm 416 moves closer to the eddy-current based position sensor 417, the effective resistive loading of the coil increases causing a reduction of the coil's Q (Q is defined in the art as the ratio of reactance to the effective series resistance of a coil). An electronic circuit can be used to measure the change in the Q of the coil and provide a signal that corresponds to the relative position of the caliper arms 401, 402. Such electronic circuits, as described for measuring changes in Q, are well known in the art.

Figure 10A:
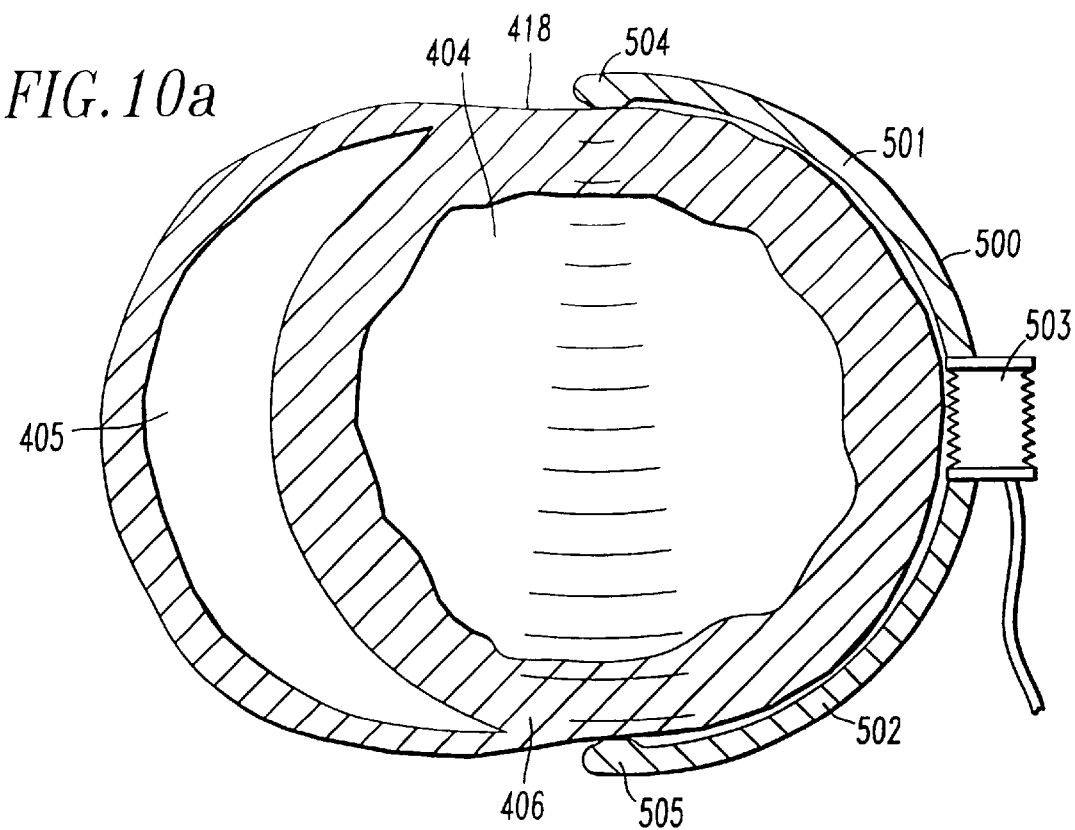
FIG. 10a is a sectional view of a sonomicrometry based heart caliper attached to a distended ventricle.
Figure 10B:
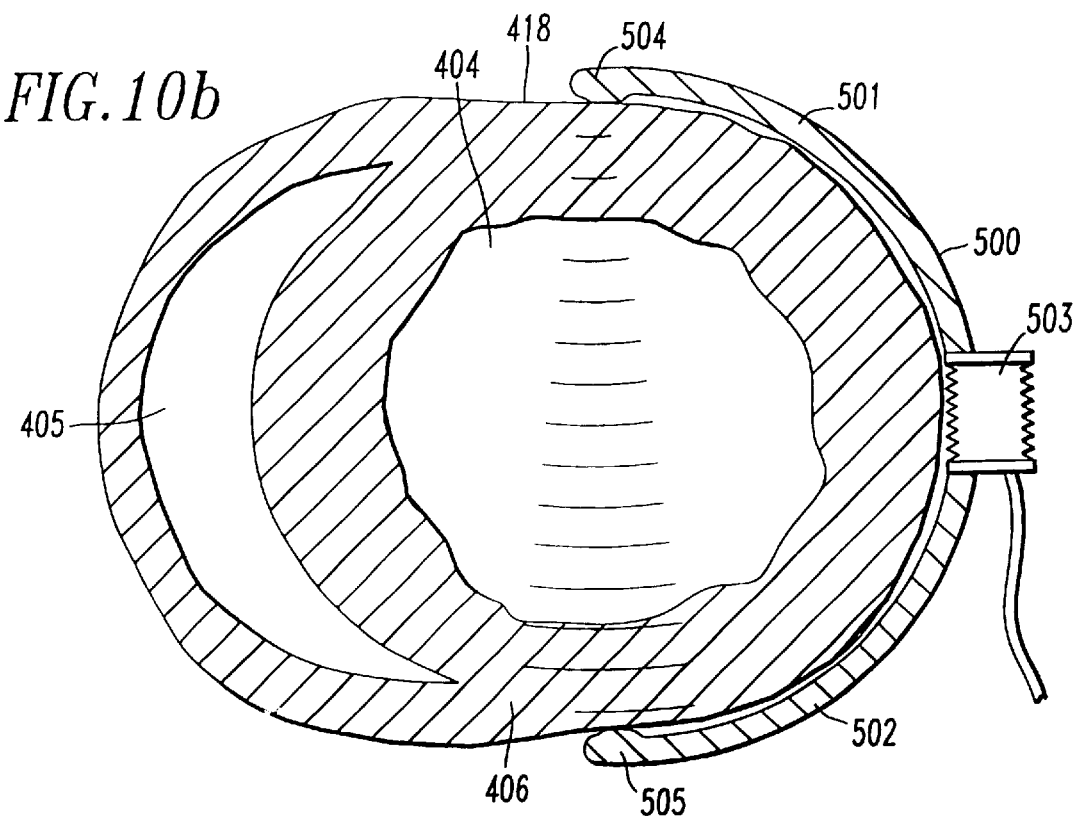
FIG. 10b is a sectional view of a sonomicrometry based heart caliper attached to a contracted ventricle.

An alternative embodiment of an electronic heart caliper 500 is illustrated in FIGS. 10a and 10b. Similarly to FIGS. 8a and 8b, FIG. 10a depicts a left ventricle that is maximally distended by the pressure of the blood contained within it and Figure 10b depicts a left ventricle that has been partially depressurized. The heart caliper 500 can have a pair of arms 501, 502 that can be suitably attached to the outside surface of the heart and pivot about a point which can preferably be located inside a hermetically sealed enclosure 503. A measure of the radial dimension of the left ventricle can be achieved by measuring the time it takes for an ultrasonic pulse to travel from a sonomicrometer transducer 504 on one caliper arm 501 to an opposing sonomicrometer transducer 505 on the other caliper arm 502. Sonomicrometer transducers suitable for use in such a heart caliper are available from companies such as Triton Technology, Inc., San Diego Calif. and Etalon, Inc., Lebanon Ind. The details of sonomicrometry are well known by those skilled in the art. It should be understood that other suitable methods for measuring the relative distention and contraction of the ventricles, such as impedance and conductance measurement of the ventricle, could be derived by those skilled in the art and the invention is not to be limited to the particular methods described.

Figure 13A:
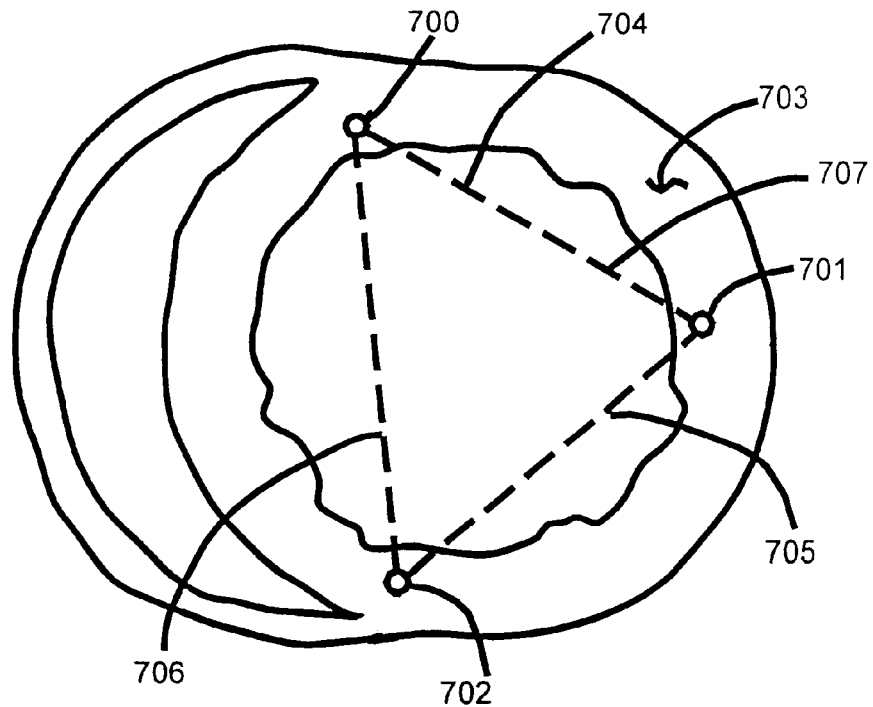
FIG. 13a is a sectional view of an alternative heart measurement apparatus for determining a cross sectional area utilizing multiple sonomicrometry based sensors associated with a distended ventricle.
Figure 13B:
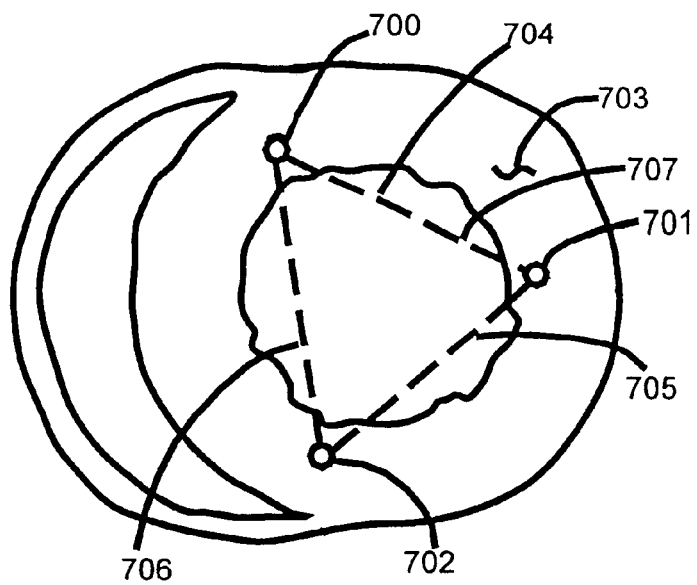
FIG. 13b is a sectional view of the heart measurement apparatus of FIG. 13a associated with a contracted ventricle.

Another heart measurement apparatus that can provide the flow rate controller with information about the dimension of the ventricle during normal distention is illustrated in FIGS. 13a and 13b. Similarly to FIGS. 8a and 8b, FIG. 13a depicts a left ventricle 703 that is maximally distended by the pressure of the blood contained within it and FIG. 13b depicts a left ventricle that has been partially depressurized. Three sonomicrometry transducers 700, 701, and 702 can be placed within the wall of the left ventricle 703. A measure of the distance 704 between transducers 700 and 701 can be achieved by measuring the time it takes for an ultrasonic pulse to travel between sonomicrometer transducers 700 and 701. A measure of the distance 705 between transducers 701 and 702 can be achieved by measuring the time it takes for an ultrasonic pulse to travel between sonomicrometer transducers 701 and 702. Likewise, a measure of the distance 706 between transducers 700 and 702 can be achieved by measuring the time it takes for an ultrasonic pulse to travel between sonomicrometer transducers 700 and 702. Sonomicrometer transducers suitable for use in such an apparatus are available from companies such as Triton Technology, Inc., San Diego, Calif. and Sonometrics Corporation, London, Ontario, Canada. The details of sonomicrometry are well known by those skilled in the art. A measure, approximately proportional to the cross sectional area of the left ventricle can be achieved by using the measured distances 704, 705, and 706 to calculate the area of the triangle 707 having vertices defined by sonomicrometry transducers 700, 701, and 702. It is preferable to place sonomicrometry transducers 700, 701, and 702 within the wall of the left ventricle 703 to most accurately approximate the cross sectional area of the left ventricular chamber while avoiding direct blood contact, however it is understood that ultrasonic transducers could also be placed on the epicardial surface of the heart or in the left ventricular chamber.

Figure 14A:
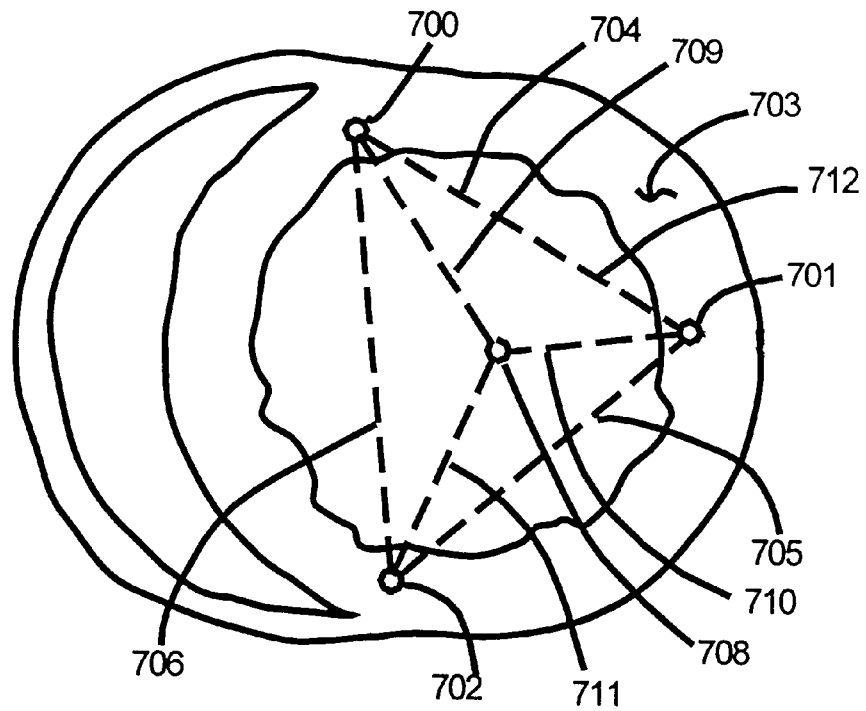
FIG. 14a is a sectional view of an alternative heart measurement apparatus for determining a volume utilizing multiple sonomicrometry based sensors associated with a distended ventricle.
Figure 14B:
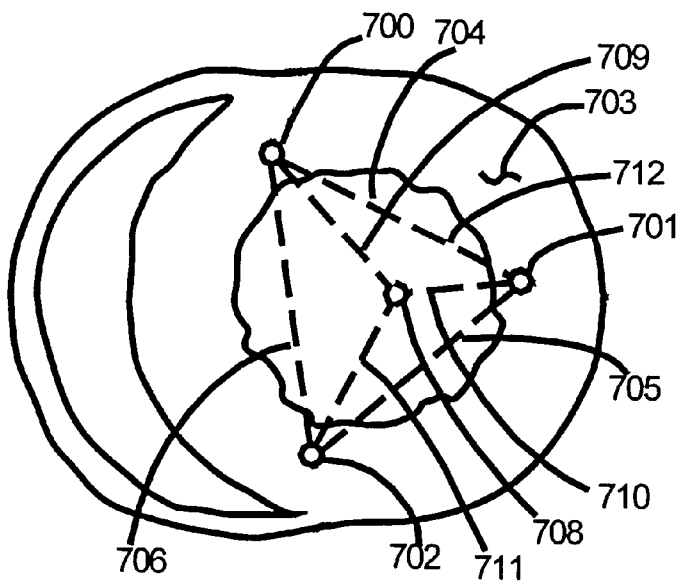
FIG. 14b is a sectional view of the heart measurement apparatus of FIG. 14a associated with a contracted ventricle.

Another heart measurement apparatus that can provide the flow rate controller with information about the dimensions of the ventricle 703 during distention and contraction is illustrated in FIGS. 14a and 14b. Similarly to FIGS. 13a and 13b, FIG. 14a depicts a left ventricle 703 that is maximally distended by the pressure of the blood contained within it and FIG. 14b depicts a left ventricle that has been partially depressurized. In addition to previously described sonomicrometry transducers 700, 701, and 702, a fourth sonomicrometry transducer 708 can be placed within the wall of the left ventricle near the apex. A measure of the distances 709, 710 and 711 between transducer 708 and transducers 700, 701 and 702 respectively can be achieved by measuring the time it takes for an ultrasonic pulse to travel between sonomicrometer transducers. A measure, approximately proportional to the volume of the left ventricular cavity, can be achieved by using distances 709, 710 and 711 along with previously described distances 704, 705 and 706 to calculate the volume of tetrahedron 712 having vertices defined by sonomicrometry transducers 700, 701, 702 and 708. It is understood that the measure of the volume of the left ventricular cavity could be made more accurate by placing additional transducers throughout the myocardium and calculating the volume of the defined polyhedron.

Figure 11:
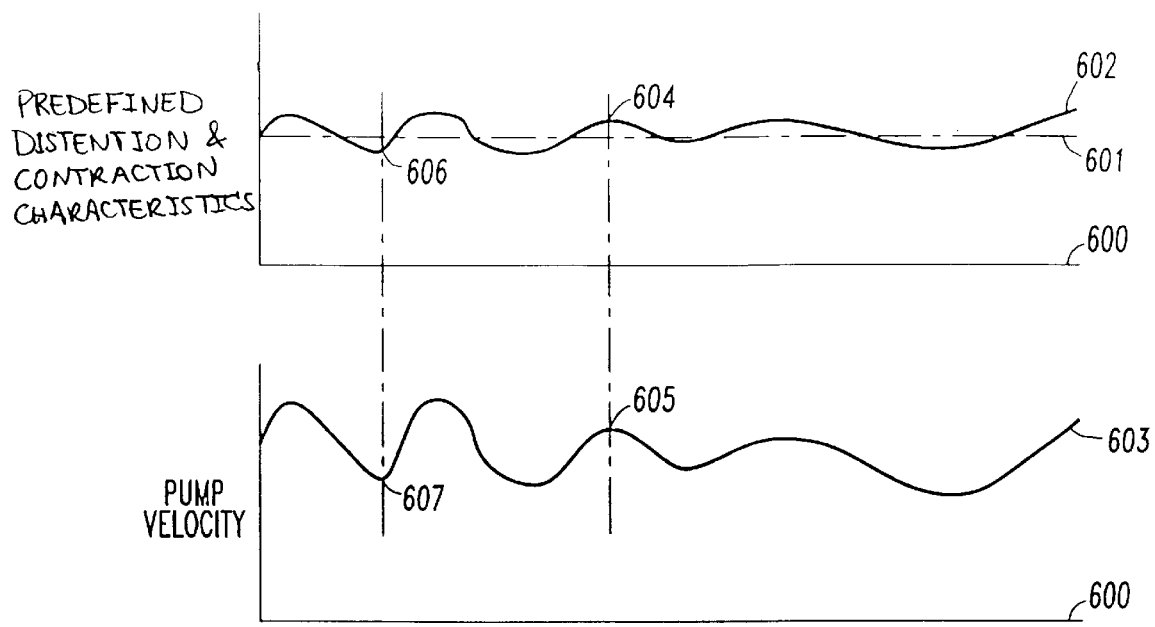
FIG. 11 is a graphical illustration of a method for controlling a steady-state flow rate of the blood pump.

One way to implement the flow rate controller, to control the flow rate of the blood pump to avoid excessive distention or contraction of the left ventricle, is graphically illustrated in FIG. 11. The x-axis' 600 represent time. Line 601 represents predefined distention and contraction characteristics of the left ventricle. The predefined distention and contraction characteristics can correspond to a radial dimension, cross sectional area or volume setpoint that is defined when the system is initially implanted and which may be periodically updated noninvasively using ultrasound imaging. Curve 602 can be representative of either the radial dimension, cross sectional area or volume of the left ventricle as sensed by either of the previously described electronic heart calipers 400, 500 or the sonomicrometry system illustrated in FIGS. 13a and 13b. Curve 603 represents the angular velocity of the disclosed centrifugal pump impeller. The flow rate of the disclosed centrifugal pump varies with the angular velocity of its impeller. When the sensed radial dimension, cross sectional area or volume exceeds the corresponding setpoint as illustrated by point 604, the angular velocity of the centrifugal pump can be increased as illustrated by point 605. The increased angular velocity of the centrifugal pump causes its flow rate to increase and more rapidly remove blood from the left ventricle, which in turn causes the radial dimension, cross sectional area or volume of the left ventricle to be reduced towards the setpoint line 601. Likewise, when the sensed radial dimension, cross sectional area or volume is less than the setpoint as illustrated by point 606, the angular velocity of the centrifugal pump can be decreased as illustrated by point 607. The decreased angular velocity of the centrifugal pump causes its flow rate to decrease and reduce the rate at which blood is removed from the left ventricle, which in turn causes the radial dimension, cross sectional area or volume of the left ventricle to increase towards the setpoint line 601.

Figure 12:
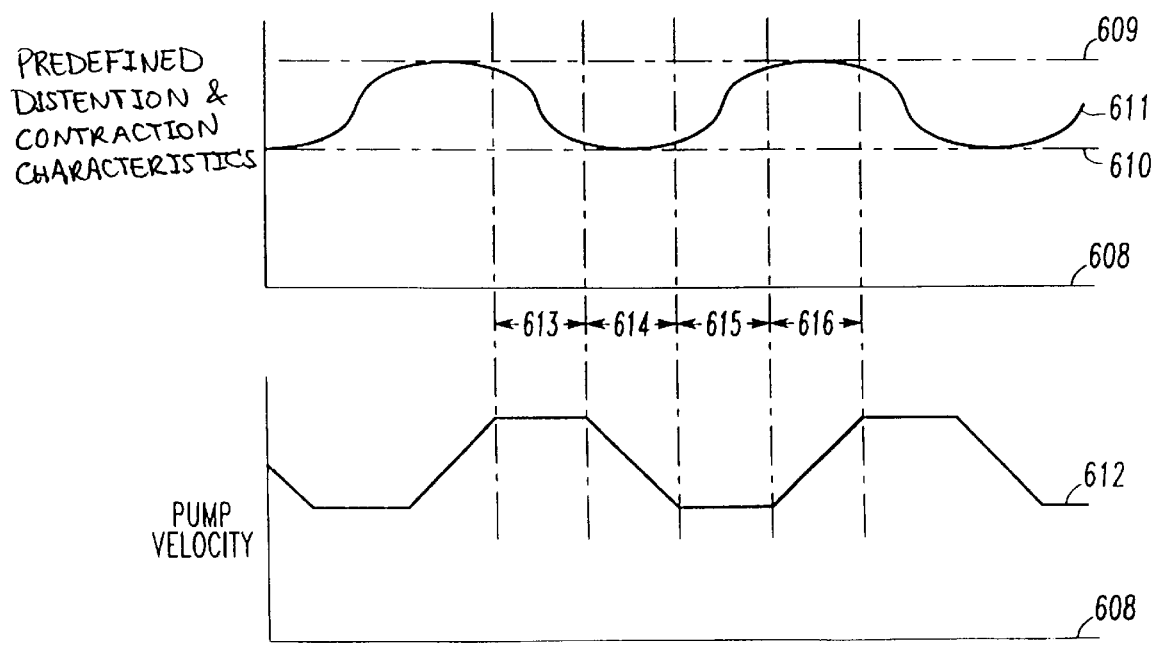
FIG. 12 is a graphical illustration of a method for controlling the flow rate of the blood pump in a pulsatile manner.

Another way to implement the flow rate controller, to control the flow rate of the blood pump to avoid excessive distention or contraction of the left ventricle, and also to create pulsatile blood flow, is graphically illustrated in FIG. 12. A pulsatile flow rate more closely mimics the blood flow characteristics of a natural heart. In FIG. 12, the x-axis' 608 represent time. Lines 609 and 610 respectively represent upper and lower left ventricular dimensional setpoints that are defined when the system is initially implanted and which may be periodically updated noninvasively using ultrasound imaging. Curve 611 can be representative of either the measured dimension, a cross sectional area or a volume of the left ventricle as sensed by either of the previously described electronic heart calipers 400, 500 or the multiple sensor apparatus illustrated in FIGS. 13*a*–13*b*. Curve 612 represents the angular velocity of the disclosed centrifugal pump impeller. The angular velocity of the centrifugal pump can be periodically increased as indicated during time period 613. The increased angular velocity of the pump during time period 613 causes blood to be more rapidly removed from the heart, which in turn causes the measured dimension, cross sectional area or volume of the left ventricle to be reduced towards the lower dimension setpoint line 610. The angular velocity of the centrifugal pump can be reduced as indicated during time period 614 once the sensed dimension, cross sectional area or volume of the left ventricle nearly equals the lower setpoint line 610. The reduced angular velocity of the pump during time period 615 causes the rate at which blood is removed from the left ventricle to be reduced, which in turn causes the sensed dimension, cross sectional area or volume of the left ventricle to increase towards the upper setpoint line 609. The angular velocity of the centrifugal pump can again be increased as indicated during time period 616 once the sensed dimension, cross sectional area or volume of the left ventricle nearly equals the upper setpoint line 609. The described pulsatile pump flow rate serves to mimic the blood flow characteristics of the natural heart.

As part of an apparatus to automatically detect and treat cardiac arrhythmias, electrodes can be placed in or on the surface of the heart and are operatively associated with the control circuitry of the apparatus. The design and operation of such automatic arrhythmia detection and treatment systems are well known in the art. In order to reduce the energy needed by such apparatus to treat fibrillation, the radial dimension of the ventricle can be purposely reduced just prior to the apparatus delivering a defibrillation pulse. The radial dimension, area or volume of the ventricle can be reduced by controlling the flow rate of the previously described blood pump such that the volume of blood within the ventricular chamber is minimized. By minimizing the volume of blood within the ventricular chamber prior to delivering a defibrillation energy pulse, a larger fraction of the supplied defibrillation energy can be delivered to the myocardium, where it is needed, and a smaller fraction of the supplied defibrillation energy is delivered to the blood, where it is unnecessary.

Although certain embodiments of the invention have been described in detail, it will be appreciated by those skilled in the art that various modification to those details could be developed in light of the overall teaching of the disclosure. In particular, it is to be understood that the blood pump flow rate control method and apparatus described herein can be equally functional with blood pumps other than magnetically suspended and operated blood pumps. For example, the ultrasonic heart measurement method and apparatus described hereinabove can be utilized to control the flow rate of any suitably controllable blood pump, notwithstanding the particular type of pump or manner of operation. Accordingly, the particular embodiments disclosed herein are intended to be illustrative only and not limiting to the scope of the invention which should be awarded the full breadth of the following claims and any and all embodiments thereof.

What is claimed is:

1. An method of controlling a blood pump flow rate comprising:
   a. measuring physical dimensions of a ventricle during at least one of distention and contraction thereof;
   b. calculating at least one of an area and a volume using said physical dimensions, said at least one of an area and a volume generally proportional to a corresponding area or volume of said ventricle;
   c. said at least one of an area and a volume indicative of said at least one of distention and contraction of said ventricle; and
   d. controlling said blood pump flow rate based on at least one of said area and said volume.

2. The method of claim 1 further comprising controlling said blood pump flow rate to produce a pulsatile flow rate.

3. The method of claim 1 wherein said measuring further comprises ultrasonically measuring a plurality of dimensions of said ventricle.

4. The method of claim 3 wherein said plurality of dimensions further comprises at least three dimensions measured in a single plane through said ventricle such that a cross sectional area is calculated.

5. The method of claim 3 wherein said plurality of dimensions are measured in more than one plane through said ventricle such that a volume is calculated.

6. An apparatus for operating a blood pump at a controlled flow rate comprising:
   a. a flow rate controller controlling said blood pump to pump blood at a flow rate;
   b. a heart measurement member operatively associated with said flow rate controller and said heart measurement member attachable to a ventricle of a heart which is assisted by said blood pump;
   c. said heart measurement member determining at least one of an area and a volume during at least one of distention and contraction of said ventricle, said at least one of an area and a volume being proportional to a corresponding area or volume of said ventricle during said at least one of distention and contraction; and
   d. said flow rate controller utilizing at least one of said area and said volume to control said flow rate.

7. The apparatus of claim 6 wherein said flow rate is a pulsatile flow rate.

8. The apparatus of claim 6 wherein said heart measurement member comprises:
   a. a plurality of ultrasonic transducers positioned at radially spaced apart locations on said ventricle; and b. said heart measurement member measuring distances between each of said plurality of ultrasonic transducers, said distances utilized to determine at least one of said area and said volume, said distances based upon an elapsed time for an ultrasonic pulse to travel between respective ones of said plurality of ultrasonic transducers.

9. The apparatus of claim 8 wherein said plurality of ultrasonic transducers further comprises at least three ultrasonic transducers positioned in a single plane through said ventricle such that a cross sectional area may be determined.

10. The apparatus of claim 8 wherein said plurality of ultrasonic transducers are positioned in at least two planes through said ventricle such that a volume may be determined.

* * * * *